(12) United States Patent
Kurtz

(10) Patent No.: US 7,807,193 B2
(45) Date of Patent: Oct. 5, 2010

(54) METHOD OF TREATING INSULIN RESISTANCE, ADULT ONSET DIABETES AND METABOLIC SYNDROME X

(76) Inventor: Seymour J. Kurtz, 630 N. State St., Apt. 2701, Chicago, IL (US) 60610

( * ) Notice: Subject to any disclaimer, the term of this patent is extended or adjusted under 35 U.S.C. 154(b) by 685 days.

(21) Appl. No.: 11/702,526

(22) Filed: Feb. 6, 2007

(65) Prior Publication Data

US 2007/0141136 A1    Jun. 21, 2007

Related U.S. Application Data

(62) Division of application No. 10/530,281, filed as application No. PCT/US03/33649 on Oct. 23, 2003, now abandoned.

(60) Provisional application No. 60/421,042, filed on Oct. 25, 2002.

(51) Int. Cl.
*A61K 9/127* (2006.01)

(52) U.S. Cl. .................... 424/450; 424/85; 530/351

(58) Field of Classification Search ................. None
See application file for complete search history.

(56) References Cited

U.S. PATENT DOCUMENTS

| | | | |
|---|---|---|---|
| 5,451,569 A | 9/1995 | Wong et al. | |
| 6,013,619 A | 1/2000 | Cochran et al. | |
| 6,261,597 B1 | 7/2001 | Kurtz | |
| 2002/0055512 A1 | 5/2002 | Marin et al. | |

OTHER PUBLICATIONS

Cantafora, A. et al, Effects of intravenous polysaturated phosphatidylcholine infusion on insulin receptor processing and lipid composition of erythrocytes in patients with liver cirrhosis. European Journal of Clinical Investigation. Aug. 1992, vol. 22, pp. 777-782, especially pp. 778-779.

Rye et al. The influence of sphingomyelin on the structure and function of reconstituted high density lipoproteins. J Biol Chem. Feb 23, 1996, vol. 271, No. 8, pp. 4243-4250.

*Primary Examiner*—Hope A Robinson
(74) *Attorney, Agent, or Firm*—Welsh Flaxman & Gitler

(57) ABSTRACT

A method of treating insulin resistance, adult onset diabetes, and metabolic syndrome X and its related complications, in a mammalian subject is accomplished by intravenously administering to a mammalian subject, a therapeutically effective amount of a liposomal suspension of lipoprotein small unilamellar vesicles (SUVs) comprising predominantly phospholipids. The liposomal suspension is administered over a period of time, whereby the levels of some or all of blood glucose, insulin, total cholesterol, LDL cholesterol, triglyceride, creatine kinase (CK), creatine kinase-MB (CK-MB), Hb-Al$_c$, lipoprotein (a), SGOT and SGPT fall back within the normal range or are significantly reduced.

10 Claims, No Drawings

METHOD OF TREATING INSULIN RESISTANCE, ADULT ONSET DIABETES AND METABOLIC SYNDROME X

This application is a Divisional of U.S. application Ser. No. 10/530,281, filed Apr. 5, 2005 now abandoned, which is the National Stage of PCT/US03/33649, filed Oct. 23, 2003 and which claims benefit to Provisional Application No. 60/421,042, filed Oct. 25, 2002.

FIELD OF THE INVENTION

The present invention relates to a method of treating insulin resistance, adult onset diabetes, and metabolic syndrome X and its related complications in a mammal using a therapeutic liposomal suspension, comprising predominantly phospholipids.

BACKGROUND OF THE INVENTION

For maintenance of homeostasis, it is critical to keep a constant supply of glucose to the cells to avoid the occurrence of dysglycemia and its related metabolic imbalances. If left ignored or untreated, metabolic dysglycemia would lead to numerous metabolic diseases, including obesity, heart disease, hypertension, diabetes, chronic fatigue, accelerated aging, degenerative disease, as well as many mental and emotional problems. For this reason, it is important to identify and, at the same time, treat this condition early before costly and disabling degenerative conditions arise that can ruin the quality of life as well as shorten it.

Dysglycemia and diabetes show up very slowly, silently and dangerously. As disclosed by the American Diabetes Association, more than a third of American adults suffering from diabetes—more than five million people—are not even aware that they have the disease. Many will learn of their condition only after they develop a severe debilitating disorder, such as heart disease, stroke, impaired vision, kidney disease, nerve damage or impotence. American Diabetes Association: Facts and Figures, 2000, at www.diabetes.org/info/facts/facts_natl.jsp.

Diabetes or diabetes mellitus is a disease that occurs when the body cannot make use of the glucose in the blood for energy because either the pancreas is not able to make enough insulin or the insulin that is available is not effective. The early signs of diabetes are glucose intolerance and insulin resistance. There are two main types of diabetes mellitus: insulin-dependent (type 1) and noninsulin-dependent (type 2 or adult onset diabetes).

A third type of diabetes is the gestational diabetes that develops only in pregnant women with no previous history of diabetes. Nearly 135,000 U.S. women develop gestational diabetes each year. Typically, gestational diabetes clears up on its own after women have delivered their babies. But studies show that about 40% of women with gestational diabetes go on to develop type 2 diabetes within 15 years (NIH Publication No. 02-3873, May 2002).

In insulin-dependent diabetes (IDDM; type I diabetes), the pancreas makes little or no insulin because the insulin-producing beta cells have been destroyed. This usually appears at any age but usually occurs between infancy and the late 30's, most typically in childhood or adolescence. Treatment consists of daily insulin injections or use of an insulin pump, a planned diet and regular exercise, and daily self-monitoring of blood glucose. If the level of insulin is too low for a long period of time, the body begins to break down its stores of fat for energy. This causes the body to release fatty acids which are then converted into ketone bodies or ketoacids that are toxic at high levels. The result is called ketoacidosis, a severe condition that may put a person into a coma if not treated right away.

In noninsulin-dependent diabetes (NIDDM; type II diabetes or adult onset diabetes (AOD)), the pancreas cannot produce enough insulin or the body tissues become resistant to insulin. Because insulin is not available or is improperly used, the blood sugar level rises above the safety level. The patient's blood sugar level often rises gradually, taking several years to reach unsafe levels and cause symptoms. Thus, in some people, where the diabetic condition has not yet developed, normal or excessive levels of insulin compensate for such resistance. Over time however, insulin production often drops and resistance worsens. About 90-95% of all diabetic people have AOD. It is more common in people over the age of 40.

AOD is caused by a complicated interplay of genes, environment, insulin abnormalities (reduced insulin secretion in the beta cells and insulin resistance in muscle cells), increased glucose production in the liver, increased fat breakdown, and possibly defective hormonal secretions in the intestine. The recent dramatic increase of this disease indicates that lifestyle factors, such as obesity and sedentary lifestyle, may be strong contributory factors in releasing the genetic elements that cause the disease.

Insulin-stimulated glucose uptake is widely variable among individuals (Stern, M. P. and Mitchell, B. D. Genetics of Insulin Resistance. In G. M. Reaven and A. Laws (eds). Insulin Resistance, The Metabolic Syndrome X, p. 3-18, Humana Press Inc., Totowa, N.J., 1999). The degree of insulin resistance observed in normal individuals can equal that seen in diabetic individuals. Hence, it is now widely known that insulin resistance precedes the development of adult onset diabetes. It is also equally essential to acknowledge that mild or even severe insulin resistance may be found in individuals who will never develop diabetes. Genetic factors contribute to this normal variation in insulin resistance. The common forms of insulin resistance include skeletal muscle insulin resistance, hepatic insulin resistance and adipose tissue insulin resistance. The entire contents of G. M. Reaven and A. Laws, (eds), Insulin Resistance, The Metabolic Syndrome X, p. 3-18, Humana Press Inc., Totowa, N.J., 1999, are incorporated herein by reference in their entirety.

The cellular response to insulin is mediated through a specific insulin receptor in the plasma membrane. When insulin activates the receptor, the•-subunit is autophosphorylated at the juxtamembrane domain, the kinase domain, and the C-terminal domain. Full receptor autophosphorylation subsequently activates the protein tyrosine kinase receptor activity, which together are necessary for the cellular response to insulin (Kahn, C. R. et al., *J. Clin. Invest.* 82:8622-8626, 1988).

Insulin resistance is an impaired response to normal levels of exogenous or endogenous insulin in cells, tissues, the liver or the entire body. It can be caused by several factors, namely: (1) obesity factors (such as elevated levels of free fatty acids and the association of insulin resistance with cytokines, e.g., resistin and leptin (Mooradian A. D., *Growth Horm. IGF Res.* 11:SupplA:S79-83, 2001; Ravussin, E. and Smith, S. R., *Ann. N.Y. Acad. Sci.* 967:363-78, 2002)); (2) proteins like calpains (Baier, L. J. et al., *J. Clin. Invest.* 106:819-21, 2000); (3) abnormal regulation of amylin and calcitonin gene-related peptide (CGRP) that affect both the circulatory and nervous system (Leighton, B. and Cooper, G. J., *Nature* 335:632-5, 1988; Haynes, J. M. et al. *Diabetologia* 40:256-61, 1997); (4) elevated levels of interleukin 6 (IL-6) and C-reactive protein (CRP) that act as inflammatory and damage markers (Hak, A.

E. et al., *J. Clin. Endocrinol. Metab.* 86:4398-405, 2001; Pickup, J. C. et al., *Diabetologia* 40:1286-92, 1997); and (5) increased level of growth hormone during puberty (Dunger, D. B. and Cheetham, T. D., *Horm. Res.* 46:2-6, 1996; Halldin, M. U. et al., *Clin. Endocrinol.* (Oxf) 48:785-94, 1998).

The main cause of death in people with AOD, regardless of sex or age, is heart disease. Other complications associated with diabetes include nerve damage (neuropathy) and vascular abnormalities in both small and large blood vessels. Heart attacks account for 60% and stroke for 25% of deaths in all diabetics. People with diabetes are at risk for heart-risk conditions that include hypertension, high triglyceride levels and lower high density lipoprotein, blood clotting problems, neuropathy, and silent ischemia. To avoid some of these complications, diabetic patients are treated with statins to improve their cholesterol and lipid levels, e.g., pravastatin (Pravachol), simvastatin (Zocor), fluvastatin (Lescol), atorvastatin (Lipitor), and rosuvastatin (Crestor). Niacin can also be administered to improve the cholesterol profile but it also increases blood sugar level.

Drug therapy is one common approach to treatment of adult onset diabetes. Oral agents such as sulfonylureas (e.g., glyburide, glipizide, glimepiride), meglitinides, biguanides, thiazolinediones, and alpha-glucosidase inhibitors, singly or combined, with or without insulin replacement therapy are used currently.

Some forms of insulin analogues may be useful for patients having adult onset diabetes. However, the possible adverse effects of insulin on weight gain and the heart are troublesome. In fact, lower mortality rates were obtained with drug treatment therapy (metformin (8%), sulfonylurea (16%) and thiazolinediones (14%) than insulin treatment (28%)).

Metabolic Syndrome X (MS-X) is a condition that promotes atherosclerosis and increases the risk of cardiovascular events through the collection of independent and related complications or disorders. This condition itself has been variously referred to as "syndrome X," "insulin resistance syndrome" (Li, C. et al., *Diabetes Care* 24: 2035-2042, 2001), "Reaven's syndrome" (Home, P., *Diabet. Med.* 6: 559-560, 1989), and "the metabolic cardiovascular risk syndrome" (Hjermann, I., *J. Cardiovasc. Pharmacol.* 20: S5-S10, 1992). The related complications or disorders of MS-X include dyslipidemia (hypertriglyceridemia and low high-density lipoprotein (HDL)-cholesterol), a prothrombotic state, type 2 diabetes (adult onset diabetes), insulin resistance/hyperinsulinemia, hypertension, and abdominal obesity. Grundy, S. M. *Am J Cardiol.* 81: 18B-25B, 1998.

Although the patient may not have any symptoms from MS-X, the attending physician could identify the following as signs of the condition: (1) elevated insulin levels, due to insulin resistance; (2) type II diabetes; (3) central obesity (a disproportionate amount of body fat in the abdominal region); (4) hyperlipidemia (high levels of fats (lipids) in the blood, which include LDL ("bad") cholesterol and triglycerides. In addition, the size of the LDLs may be smaller than usual, which is more likely to promote atherosclerosis); (5) low level of HDL ("good") cholesterol; (6) hypertension (high blood pressure); (7) elevated levels of blood factors that promote blood clotting, such as plasminogen activator inhibitor-1 (PAI-1) and fibrinogen; (8) hyperuricemia (high levels of uric acid in the blood); and (9) microalbuminuria (small amounts of the protein albumin, found on urine tests). Grundy S. M., *Am. J. Cardiol.* 83: 25F-29F, 1999.

Independently, each of these complications or disorders promotes atherosclerosis. However, when grouped together, they are increasingly atherogenic and enhance the risk of cardiovascular disease (CVD) at any low density lipoprotein cholesterol level. In addition to increasing a patient's risk of CVD, MS-X may enhance the development of stroke, type 2 diabetes (Lebovitz, H. E., *Exp. Clin. Endocrinol. Diabetes* 109: S135-S148, 2001), diabetic nephropathy, retinopathy, and distal neuropathy (Isomaa, B. et al., *Diabetologia* 44:1148-1154, 2001).

Using the above-mentioned features, one estimate suggests that as many as 50 to 75 million people in the United States may exhibit significant signs of MS-X by 2010. Hansen, B. C., *Ann. NY Acad. Sci.* 892: 1-24, 1999.

According to the World Health Organization (WHO) guideline, an individual is diagnosed to have MS-X if the features are present: a) hypertension (>140 mm Hg systolic or >90 mm Hg diastolic); (b) dyslipidemia, defined as elevated plasma triglycerides (150 mg/dL) and/or low high-density lipoprotein (HDL) cholesterol (<35 mg/dL in men, <39 mg/dL in women) concentrations; 3) obesity, defined as a high body mass index (BMI) (30 kg/m$^2$) and/or a high waist-to-hip ratio (>0.90 in men, >0.85 in women); and 4) microalbuminuria (urinary albumin excretion rate•20•g/min). See WHO-International Society of Hypertension Guidelines for the Management of Hypertension. Guidelines Subcommittee. *J. Hypertens.* 17:151-183, 1999. By this standard, individuals with type 2 diabetes must meet only 2 of the criteria in order to be diagnosed with MS-X.

A similar guideline, established by the National Cholesterol Education Program (NCEP ATP III study) establishes that a person would have MS-X, if 3 or more of the following risk factors are present: (1) a waist circumference >102 cm (40 in) for men or >88 cm (37 in) for women; (2) a triglyceride level•150 mg/dL; (3) an HDL cholesterol level <40 mg/dL for men or <50 mg/dL for women; (4) blood pressure•130/•85 mm Hg; or (5) a fasting glucose•110 mg/dL. See *JAMA* 285: 2486-2497, 2001.

These guidelines assert that abdominal obesity rather than elevated BMI is more highly associated with MS-X and suggest that all patients with abdominal obesity should be evaluated for the possibility of this syndrome. In addition, ATP III guideline has a lower diagnostic threshold level than that of WHO for certain characteristics (i.e., HDL cholesterol and hypertension). Therefore, a higher proportion of the population meets the ATP III standard for the diagnosis of MS-X.

The central features of MS-X are all highly related, entail numerous physiological systems, and reveal a complex multifactorial etiology. In dyslipidemia, also known as the lipid triad, other lipid abnormalities, such as moderately raised (often high-normal) triglycerides, increased preponderance of small, dense LDL particles, and low levels of HDL cholesterol are included. Grundy, S. M. *Circulation* 95: 1-4, 1997. Dyslipidemia and insulin resistance are related metabolic conditions. Haffner, S. M. *Am. J. Cardiol.* 83: 17F-21F, 1999 and Ginsberg, H. N. and Huang, L. S., *J. Cardiovasc. Risk* 7: 325-331, 2000.

With respect to a prothrombotic state, insulin resistant patients often experience changes in coagulation factors that may promote arterial thrombosis and inflammation. Grundy, S. M. et al., *Circulation* 100: 1134-1146, 1999. A procoagulant state may increase the formation of atherosclerotic plaques and the size of thrombi following the rupture of plaques. Commonly identified conditions in the MS that are related to a prothrombotic state include activation of endothelial cells, promotion of LDL oxidation, enhanced platelet aggregation, activation of factor VII, increased levels of factor IX, factor X, and prothrombin, and increased concentrations of PAI-1. Peroxisome proliferator-activated receptor-α (PPAR-α), a major regulator of intra- and extracellular lipid metabolism, may play a role in atherogenic dyslipidemia and inflammation. Gervois, P. et al., *Clin. Chem. Lab. Med.* 38: 3-11, 2000. Activation of the PPAR-α ligand-binding domain may assist fatty acid metabolism in the liver by promoting transcription of certain target genes, such as fatty acid binding protein. In addition, PPARs may play a central role in regulating the interaction between HDL cholesterol and apolipoprotein (apo) B-containing lipoproteins. Pineda, T. I., et al., *Curr. Opin. Lipidol.* 10: 151-159, 1999.

Overproduction of insulin leads to hypertension. WHO guidelines suggest that patients receiving anti-hypertensive treatment and/or having elevated blood pressure (>140 mm Hg systolic or >90 mm Hg diastolic) are at risk for MS. *J. Hypertens.* 17: 151-183, 1999. Hypertension has been well established as a metabolic disorder and is predictive of insulin resistance. Lind, L. and Lithell, H. *Am. Heart J.* 125: 1494-1497, 1993. As many as 50% of the anti-hypertensive patients have comorbid insulin resistance and hyperinsulinemia. McLaughlin, T. and Reaven, G., *Geriatrics* 55: 28-35, 2000. The use of an appropriate pharmacologic agent to reduce blood pressure may lessen the signs of insulin resistance in patients who exhibit both conditions. Lowering elevated blood pressure may also improve a patient's lipid profile. Weidmann, P. et al., *Am. Heart J.* 125: 1498-1513, 1993.

Increased blood pressure independently increases the risk of atherosclerosis, presumably by promoting the entry of LDL into the subendothelial space, and may exacerbate other metabolic abnormalities. Hormstra, G. et al., *Br. J. Nutr.* 80:S113-S 146, 1998.

For diagnosis of MS-X, a variety of blood test are used to measure levels of glucose, insulin, triglycerides, cholesterol, uric acid, fibrinogen and PAI-1. In addition, blood pressure and body weight should be measured and evaluated.

Currently, the only known treatment strategies that addresses all the factor of MS-X are weight loss and exercise. Medications are given but physicians would usually encourage the MS-X patients to change their life style such as decreasing the amount of fats and oils in their diet, avoiding concentrated sweets, quitting smoking and avoiding excessive alcohol use.

Besides the above-mentioned strategies, several groups have disclosed the use of specific drugs to treat MS-X and its related complications. Below is a brief summary of their disclosures.

U.S. Pat. No. 6,166,049 discloses a method for the treatment or prophylaxis of syndrome X in a human or non-human mammal by administering an effective, non-toxic and pharmaceutically effective amount of an agonist of peroxisome proliferator-activator receptor-• and -• (PPAR-• and PPAR-•). The inclusion of PPAR-• in a PPAR-• anti-hyperglycaemic agent will result in a reagent with enhanced therapeutic potential in the syndrome X etiology due to an enhanced hypolipaedemic effect. The invention provides a prophetic example relating to the efficacy of the compounds on blood glucose and plasma lipids in a genetically diabetic mouse.

U.S. Pat. No. 6,197,765 discloses a treatment for MS-X and its related complications, including diabetes complications, by administering a dose of diazoxide to inhibit the release of insulin and proinsulin, lower weight, reduce levels of circulating cholesterol and triglycerides, lower blood pressure and prevent and reverse diabetic complications.

U.S. Pat. No. 6,410,339 discloses the use of synthetic cortisol agonists that have glucocorticoidal and/or mineral corticoidal effects, e.g., dexamethasone, for preparing a system to diagnose MS and its related conditions such as belly fatness, insulin resistance including risk of developing senile diabetes, i.e., diabetes type II, high blood fats and high blood pressure. The dose of cortisol agonist is in an interval where a difference is obtained in the inhibitory effect of the auto-production of cortisol in individuals suffering from MS, compared to normal values.

U.S. application serial No. 20020165237 by Fryburg et al. teaches the use of selective cyclic guanosine monophosphate (cGMP) specific phosphodiesterase type 5 inhibitors, such as sildenafil, for the treatment of insulin resistance syndrome (IRS). Sildenafil has been shown to be effective in the treatment of male erectile dysfunction. Sildenafil increases the intracellular concentrations of nitric oxide (NO)-derived cGMP. This accumulation would amplify the vasodilatory, metabolic, and anti-atherogenic effects of the available nitric oxide and insulin. According to the inventors, such treatment may lead to clinically relevant improvements in blood pressure and/or blood sugar and/or lipids and/or uric acid, and/or procoagulant factors. This treatment can occur alone or in combination with other therapeutics that improve IRS which, in turn, should reduce the risk of the development of cardiovascular disease in some patients, as well as other complications of individual disorders (including, but not limited to diabetic neuropathy, nephropathy, and retinopathy).

U.S. application serial No. 20020037861 A1, by Plata-Salaman et al., discloses the use of anticonvulsant derivatives in preventing the development of type II diabetes mellitus and syndrome X. One of the anti-convulsant derivatives, 2,3:4,5-bis-O-(1-methylethylidene)-β-D-fructopyranose sulfamate (known as topiramate), has been demonstrated in clinical trials of human epilepsy to be effective as adjunctive therapy or as monotherapy in treating simple and complex partial seizures and secondarily generalized seizures. Using a homozygous diabetic mouse model (ob/ob), treatment with topiramate resulted to a significantly lower levels of blood glucose, triglycerides, and insulin and glycosylated hemoglobin than in control ob/ob mice not given topiramate. According to the inventors, these findings demonstrate that topiramate can reduce or prevent pathophysiological signs associated with syndrome X. In addition, the amelioration of diabetic condition by topiramate is not dependent on a reduction in body weight.

Although drug therapy has proven to be effective in reducing and treating insulin resistance, adult onset diabetes, and MS-X and its related complications, it leads to side effects, such as weight gain, water retention, slight risk of cardiac events and hypoglycemia, gastrointestinal problems including nausea, flatulence, and diarrhea, lactic acidosis, reduced absorption of vitamin B12 and folic acid, and reduced iron absorption.

Accordingly, there is a need to provide an improved method of treating the above-mentioned conditions that avoids or minimizes these side effects. There is a continuing need to provide an early method for treating these conditions to avoid the emergence of costly and disabling degenerative conditions, as described above.

SUMMARY OF THE INVENTION

The present invention is based on the discovery that treatment of mammalian subjects with intravenously administered liposomes of the type described herein results in a reduction of insulin resistance and improvement of symptoms of adult onset diabetes, and metabolic syndrome X and its related complications, with negligible or no side effects.

In one general embodiment, the method is used to treat a mammalian subject having the above-mentioned conditions, as evidenced by the reduction of one or more of blood glucose, insulin, total cholesterol, LDL cholesterol, triglyceride, creatine kinase (CK), creatine kinase-MB (CK-MB), Hb-Al$_c$, lipoprotein (a), SGOT and SGPT of the mammalian subject. In a preferred embodiment, the method comprises intravenously administering to a mammalian subject a therapeutically effective amount of liposomal suspension of lipoprotein small unilamellar vesicles (SUVs) comprising predominantly phospholipids.

In one aspect, the liposomal suspension of lipoprotein SUVs comprise phospholipids selected from the group consisting of phosphatidylcholine, phosphatidylglycerol and phosphatidylserine. In another aspect, the phosphatidylcholine is 1-palmitoyl, 2-oleoyl phosphatidylcholine and 1-palmitoyl, 2-linoleoyl phosphatidylcholine and can be derived from eggs.

In another embodiment, the lipoprotein SUVs comprise predominantly of phosphatidylcholine having a transition temperature of less than about 37° C., preferably about −10 to 24° C. The liposomal suspension of lipoprotein SUVs further comprises sphingomyelin, cholesterol or other sterols, in an amount less than about 40 mole percent. In yet another embodiment, the lipoprotein SUVs are empty.

In one embodiment, the liposomal suspension is administered one to three times per week to a mammalian subject having the above-described conditions at a dose of about 50 mg-1 g total lipid/kg body weight, preferably at a dose of about 200-450 mg total lipid/kg body weight. The administration can be achieved via intravenous injection or intravenous infusion.

The features and details of the invention will become more apparent and appreciated by one skilled in the art to which this invention pertains from the following detailed description of the invention.

DETAILED DESCRIPTION OF THE INVENTION

I. Definitions

In the description that follows, a number of terms are used extensively. The following definitions are provided to facilitate understanding of the invention.

Unless otherwise specified, "a" or "an" means "one or more."

"Mammalian subject" refers to both a veterinary animal or a human.

"Glycosylated or glycated haemoglobins (Hb-$A_{1c}$)" refers to normal haemoglobin to which a glucose molecule becomes added in a non-enzymatic manner. The percentage haemoglobin that is glycated is directly proportional to the time that red blood cells have been exposed to glucose, and to glucose concentrations. Measurement of the glycated haemoglobin fraction gives an integrated picture of the average blood glucose concentration during the half life of the cells—that is over the last 60 days. Hb-$A_{1c}$ is usually given as a percentage of the total hemoglobin. Hb-$A_{1c}$ levels in individuals with normal glucose tolerance have a normal range of 4.3% to 6.3% (Peters, A. L. et al. J. Am. Med. Assoc. 276:1246-52, 1996).

"Serum Glutamic-Oxaloacetic Transaminase" ("SGOT") or Aspartate Aminotransferase" ("AST") is an enzyme found primarily in the liver, heart, kidney, pancreas, and muscles. It is elevated in patients with muscular disease, myocardial injury and renal infarction. Decreased levels can be found in Vitamin B deficiency and pregnancy. The normal value range is 0-50 U/l . The optimal adult reading is 21 U/l.

"Serum Glutamic-Pyruvic Transaminase" ("SGPT") or Alanine Aminotransferase" ("ALT") is an enzyme found primarily in the liver but also in the heart and other tissues. Decreased SGPT in combination with increased cholesterol levels is seen in congested liver cases. Increased levels are seen in mononucleosis, alcoholism, liver damage, kidney infection, chemical pollutants or myocardial infarction. The normal value range is 0-41 U/l. The optimal adult reading is 24 U/l.

"C-Reactive Protein" ("CRP") is a protein present in many acute inflammatory conditions and is a significant risk factor in cardiovascular disease. Higher levels of CRP may play a role in abdominal obesity and the onset of type II diabetes or AOD. The normal range for CRP is 0-0.5 mg/dl.

"Creatine Kinase" ("CK") is an enzyme found in the heart, brain, and skeletal muscle. Blood levels of CK rise when the muscles or heart cells are injured. CK occurs in three major forms, called isoenzymes, namely: (1) CK-MB (found mostly in the heart muscle); (2) CK-BB (found mostly in the brain); and (3) CK-MM (found in the heart and other muscles). CK-MB levels, along with total CK, are tested in persons who have chest pain to determine whether they have had a heart attack. Since a total CK would indicate damage to either a heart or other muscles, a high CK-MB suggests that the damage was to the heart muscle. The normal ranges for CK and CK-MB are 0-195 U/l and 0-24 U/l, respectively.

"Glucose intolerance" refers to the inability of the body to utilize glucose in blood circulation. Glucose intolerance is increased in diabetes mellitus and in endocrine disorders such as polycystic ovary syndrome.

"Insulin" refers to the hormone that helps shuttle glucose from the blood to the cells. The beta cells in areas of the pancreas called the islets of Langerhans usually make insulin.

"Insulin sensitivity" (or "insulin receptivity") is the normal and preferable state, in which the body's cells remain sensitive (or receptive) and responsive, to insulin action.

"Insulin resistance" refers to a state wherein abnormally high glucose levels trigger an increase in insulin to remove this sugar from the bloodstream. Often, the body's cells start to ignore high insulin levels and therefore become resistant to the hormone's effects. Insulin resistance allows glucose levels to rise and stay high. However, it does not always lead to diabetes.

Hypertension is defined as elevated blood pressure.

Dyslipidemia is defined as elevated plasma triglycerides and/or low high-density lipoprotein (HDL) cholesterol concentrations.

Obesity is defined as a high body mass index (BMI) and/or a high waist-to-hip ratio.

"Lipid replacement therapy" refers to a therapy in which the treatment modifies the composition of the cell membranes in both tissue cultures as well as the whole organism particularly, but not limited to, the red blood cells, blood vessels, heart cells and kidney cells in such a way as to cause the cholesterol to phospholipid mole ratio as well as the sphingomyelin to phosphotidylcholine mole ratio to decrease and revert to values found in young cells or tissues of young organisms.

"Empty" liposomes refers to liposomes that do not contain entrapped or encapsulated drug.

"Small unilammelar vesicles (SUVs)" refer to small single-bilayer liposomes having particle sizes ranging predominantly between 20 and 120 nm. The SUVs of the present invention can be empty. They comprise phospholipids, preferably phospholipids selected from the group consisting of phosphatidylcholine, phosphatidylglycerol, and phosphatidylserine. The phosphatidylcholine may be an egg phosphatidylcholine.

The phrase "milligram or gram total lipid/kg body weight" refers to the amount of total lipids in milligrams or grams comprising the lipoprotein SUVs per kilogram body weight. Total lipids may include phosphatidylcholine, sphingomyelin, cholesterol, phosphatidylserine, phosphatidyglycerol or any other lipids described in the present invention.

A "significant improvement" in a disease state is a measurable degree of improvement, as indicated by either a clinical or biochemical indicator, in the disease state. Typically, a significant improvement in a disease state is one which results in an improvement of a parameter with a known correlation to the disease state of at least five percent.

The terms "elevated blood glucose, insulin, total cholesterol, LDL cholesterol, and triglyceride", as used herein, refer to concentrations of blood glucose, insulin, total cholesterol, LDL cholesterol, and triglyceride that are on average elevated above the normal average concentrations when measured at various times over the course of a week. A normal range for glucose is generally between 55-115 mg/dl; for triglyceride, 0-200 mg/dl; for total cholesterol, 100-200 mg/dl; and for LDL cholesterol, 0-155 mg/dl.

"Oral glucose tolerance test (OGTT)" refers to a two to three-hr glucose tolerance test that measures blood glucose levels four to five times over a 2-3-hour period. The patient is administered an oral dose of glucose solution (75 to 100 grams of an extremely sweet drink), which should cause glucose levels to rise in the first hour, and then fall back to normal within two to three hours as the body produces insulin to normalize glucose levels. This test us used to confirm a diagnosis of diabetes mellitus or gestational diabetes (and to diagnose other metabolic diseases).

OGTT is a more sensitive test than the fasting plasma glucose test, and involves multiple blood draws to monitor insulin production, it can often detect cases of mild diabetes that may be missed by the fasting test. The most commonly used test protocols include the Wilkerson point system; the Fajans-Conn system, or the National Institutes of Health (NIH) system. On average, normal glucose levels typically peak at 160-180 mg/dl from 30 minutes to 1 hour after administration of the oral glucose dose, and should then return to fasting levels of 140 mg/dl or less within a 2 to 3 hour period. Factors such as age, weight, and race can influence results, as can recent illnesses and certain medications. For example, older individuals will have an upper limit increase of 1 mg/dl in glucose tolerance for every year over age 50. Glucose levels that quickly rise above normal levels (i.e., 200 mg/dl or higher) and take longer to normalize usually indicate diabetes mellitus.

Insulin resistance should be diagnosed by measuring insulin levels—fasting levels alone, or with a glucose tolerance test plus insulin (sometimes called an IGTT). Diabetes may be diagnosed based on blood glucose levels alone.

| Oral Glucose Tolerance Test - Glucose and Insulin Values | | | |
|---|---|---|---|
| Time (hour) | Normal Glucose Values | Normal Insulin Values | Interpretation of Results |
| Fasting | <126 mg/dl | <10 mIU/ml | Normal glucose results are 70-90, 111 or over is impaired, 126 or over is diabetic. Insulin levels above 10 show insulin resistance. |
| 0.5 | <200 mg/dl | 40-70 mIU/ml | A truly normal glucose response will not exceed 150. |
| 1 | <200 mg/dl | 50-90 mIU/ml | Some want to lower the threshold on glucose to <180 to identify early stages of diabetes. Insulin >80 shows insulin resistance, or a level 5 times that of the fasting level (i.e., a fasting of 11 followed by a 1 hour >55) |
| 2 | <140 mg/dl | 6-50 mIU/ml | A truly normal glucose response is 110 or lower. Insulin >60 is IR. |
| 3 | <120 mg/dl | | |
| 4 | <120 mg/dl | | |

While not wishing to be bound by a particular theory, the present inventor discovered that a liposomal suspension known to be effective in treating conditions associated with aging, such as heart disease, is also useful in treating insulin resistance, adult onset diabetes and metabolic syndrome-X and its related complications. The treatment uses a similar protocol to that which is known in the art. However, this treatment must be adapted to the treatment of insulin resistance, adult onset diabetes and metabolic syndrome X and its related complications, as would be apparent to the ordinary skilled physician.

II. Preparation of Liposomal Composition

The present invention involves intravenous administration of a therapeutic liposomal suspension to a subject having insulin resistance, adult onset diabetes, and metabolic syndrome X and its related complications. The liposomal suspension comprises lipoprotein small unilammelar vesicles (SUVs), comprising predominantly phospholipids selected from the group consisting of phosphatidylcholine, phosphatidylglycerol, and phosphatidylserine. The phosphatidylcholine may be an egg phosphatidylcholine. Preparation of the lipoprotein SUVs of the present invention is illustrated in the Examples and in the sections which follow.

A. Preparation of Liposomes: Composition

Lipoproteins are high molecular weight particles that are primarily responsible for lipid transport, namely of triglycerides and cholesterol in the form of cholesteryl esters, through the plasma. Five major classes of naturally-occurring lipoproteins are known to circulate in plasma, each differing in lipid composition, apoprotein composition, density, size, and electrophoretic mobility.

Each lipoprotein particle is composed of a non-polar core region, a surrounding phospholipid surface coating containing small amounts of cholesterol, and exposed at the surface. In vivo, the lipoprotein particles can become associated with apoproteins, e.g., apoproteins A and C, that are responsible for binding to receptors on cell membranes and directing the lipoprotein carrier to its intended site of metabolism.

In one preferred embodiment, described and used in the examples below, the lipoprotein SUVs comprise predominantly (more than 50 mole percent, preferably more than 80-90 mole percent) of phosphatidylcholine (PC) having a phase transition temperature less than about 37° C., preferably about −10 to 24° C., e.g., below about 5° C.

PC phospholipids include those phospholipids having a choline moiety and where the fatty acid chain portion of the phospholipid may vary in length and degree of unsaturation. In addition, PC phospholipids also include synthetic PCs that are not crystalline at body temperature (e.g., those containing at least one double bond) yet are resistant to oxidation (e.g., those that do not have double bands, such as 1-palmitoyl, 2-oleoyl PC (POPC)). PC phospholipids may further include natural or synthetic phospholipids, alone or in mixtures having supplemented or replaced hydrophobic or amphipathic material that still maintains a liposomal or micellar structure.

One preferred vesicle composition includes egg PC, which has a transition temperature of −5° C., that contains predominantly 1-palmitoyl, 2-oleoyl PC and 1-palmitoyl, 2-linoleoyl PC. Alternatively, phosphatidylcholine may be isolated from rat liver (Newman, H. A. I. et al., *J. Lipid Res.* (1961) 2:403-11), followed by purification on alumina (Shinitzky, M. et al., *J. Biol. Chem.* (1974) 249:2652).

The lipoprotein SUVs may be composed entirely of egg PC, or may contain other lipid components which (i) are not immunogenic, (ii) do not contribute a significant portion, i.e., more than 25-50 mole percent, of lipids with high phase transition temperature. Additional components may include negatively charged lipids, such as phosphatidylglycerol (PG) or phosphatidylserine (PS). Addition of PG would make the SUVs negatively charged or charge other components of the lipoprotein SUVs to prevent aggregation during storage. If the lipoprotein SUVs is composed entirely of PC, the mole percentage of PG and PS is less than 1% with respect to PC. However, if PC is not a major component of the lipoprotein SUVs, the mole percentage of PG and PS would be more than 1% with respect to PC. The lipoprotein SUVs may also encompass sphingomyelin (SM), cholesterol or other sterols, in an amount preferably less than about 40 mole percent. Other components may also include diacylglycerol, phosphatidylinositol, oxidized lipids, lysophosphatidylcholine, and proteins, such as phospholipid transfer proteins (PLTP; see *Biomembranes Structural and Functional Aspects*, M. Shinitzky (ed.), 1994, at page 40) and amniophospholipid translocase (either as a 116-kd $Mg^{2+}$ ATPase (Morot, G. et al., *Biochemistry* 28: 3456, 1989; Morot, G. et al., *FEBS Lett.* 266: 29, 1990) or as a 32-kd protein (Schroit, A. J. et al., *Biochim. Biophys. Acta* 1071: 313, 1991)).

Lipid protective agents, such as •-tocopherol, •-tocopherol acetate, or •.-tocopherol succinate, may also be included in the lipids forming the lipoprotein SUVs, to protect the lipid components against free radical damage. Typically such agents are included at a mole percentage between about 0.5% and 2%. It may be advantageous to add•-tocopherol to the lipoprotein SUVs to maintain a balance between vitamin E and polyunsaturated lipids in the lipoprotein SUVs. Alternatively, the lipoprotein SUVs can be prepared and stored in an inert gas atmosphere, e.g., nitrogen, argon and the like.

B. Preparation of Unsized Liposomes

A variety of methods for producing lipoprotein SUVs are available, and these have been extensively reviewed (Szoka, F. et al., *Ann. Rev. Biophys. Bioeng.* (1980) 9:467). In general, these methods produce lipoprotein SUVs with heterogeneous sizes from about 0.02 to 10 microns or greater. As will be discussed below, lipoprotein SUVs which are relatively small and well-defined in size are preferred for use in the present invention, hence a second processing step for reducing the size and size heterogeneity of liposomal suspensions will usually be required.

In one preferred method for forming the initial liposome suspension as described in Example 1, the vesicle-forming lipids are taken up in a suitable organic solvent system, preferably in a siliconized glass vessel, and dried in vacuo or under an inert gas to form a lipid film. An aqueous suspension medium, such as a sterile saline solution, is added to the film, and the vessel is agitated (e.g., on a shaker or using a sonicator) until the lipids have hydrated to completion, typically within about 1-2 hours. The amount of aqueous medium added is sufficient to produce a final liposome suspension containing preferably between about 5 and 30 g total lipid per 100 ml media, preferably 10 g total lipid per 100 ml media.

During the hydration stage, the lipids hydrate to form multilamellar vesicles (MLVs) with sizes ranging between about 0.5 microns to about 10 microns or larger. In general, the size distribution of MLVs can be shifted toward slightly smaller sizes by hydrating the lipids under more vigorous agitation conditions.

The aqueous medium used in forming the lipoprotein SUVs may contain water-soluble agent(s) which enhance the stability of the liposomes upon storage. A preferred stabilizing agent is an iron-specific trihydroxamine chelating agent, such as desferrioxamine. The use of this compound in reducing lipid peroxidation and free radical damage in drug-containing liposomes has been reported in U.S. Pat. No. 4,797,285. Briefly, it was shown that the combination of a lipophilic free-radical quencher, such as •-tocopherol, and the water-soluble chelator gave substantially better protection against lipid peroxidation damage than did either of the protective agents alone. The chelator is included in the aqueous medium in niolar excess of the amount of free iron in the medium. Typically, a chelator concentration of between about 10-200 micromolar is sufficient for reducing lipid peroxidation and free radical damage.

C. Sizing Liposomes: SUV Preparation

The suspension of lipoprotein SUVs prepared as described above is preferably further treated to produce liposomes having a desired size and size homogeneity.

The liposome suspension is generally sized to achieve a selective size distribution of vesicles in a size range less than about 1.2 micron and preferably less than about 0.8 microns. Liposomes in this size range can be readily sterilized by filtration through a depth filter. Smaller vesicles also show less tendency to aggregate on storage, thus reducing the potential for serious vascular blockage problems upon intravenous administration of the final liposomal composition of the present invention. Finally, lipoprotein SUVs which have been sized down to the submicron range possess more uniform biodistribution and drug clearance characteristics.

Preferred lipoprotein SUVs, i.e., single-bilayer liposomes, have sizes between about 0.02 to 0.12 microns. SUVs have been shown to possess relatively long blood circulation half lives, when administered intravenously, as described in U.S. Pat. No. 6,235,308, filed Jun. 10, 1994. Briefly, as described therein, plots of liposome retention in the bloodstream, measured up to 1,000 minutes after IV injection, revealed that significant quantities of liposomes remained in the bloodstream even at 1,000 minutes.

Several techniques are available for reducing the sizes and size heterogeneity of liposomes, in a manner suitable for preparing the lipoprotein SUVs of the present invention. Ultrasonic irradiation of a liposome suspension either by bath or probe sonication produces a progressive size reduction down to SUVs.

Homogenization is another method which relies on shearing energy to fragment large liposomes into smaller ones. In a typical homogenization procedure, MLVs are recirculated through a standard emulsion homogenizer until selected liposome sizes, typically less than 0.1 microns, are observed.

Extrusion of liposomes through a small-pore polycarbonate membrane is an effective method of reducing liposome size down to a relatively well-defined size distribution. An average range is between about 0.03 and 1 micron, depending on the pore size of the membrane, such as described in Example 2. Typically, the suspension is cycled through the membrane several times until the desired liposome size distribution is achieved. The lipoprotein SUVs may be extruded through successively smaller pore membranes, to achieve a gradual reduction in liposome size.

Liposome particle sizes can be determined by a number of techniques including electron microscopy, comparative chromatography (Bisgaier, C. L. et al., *J. Biol. Chem.* (1989) 264(2):862-866) and quasi-elastic light scattering.

The size-processed liposome suspension may be readily sterilized by passage through a sterilizing membrane having a particle discrimination size of about 0.2µ, such as a conventional 0.22µ depth membrane filter. If desired, the liposome suspension can be lyophilized for storage and reconstituted shortly before use.

III. Methods of Treating Insulin Resistance, Adult Onset Diabetes Disease, and Metabolic Syndrome X and Its Related Complications This section describes treatment methods which involve intravenous administration of the liposomal suspension described above. In all of these methods, the suspension is administered intravenously at a dose and dosing frequency effective to produce a desired improvement in the treated condition.

A preferred dosing frequency is one, two or three times per week. The dosing periods, e.g., two weeks, may be interrupted by a wash-out period, typically of 1-4 weeks. The treatment, e.g., involving repeating dosing and wash-out periods, may continue over an extended period of several months or more.

In a preferred embodiment, the liposome suspension is administered one to three times per week, at a dose of about 50 mg-1 g total lipid/kg body weight per dose, preferably between about 200-450 mg total lipid/kg body weight per dose. Administration may be by i.v. (intravenous) injection, or i.v. drip (infusion). The lipoprotein SUVs may be suspended in sterile saline or in a nutritional or drug-containing buffer or medium, such as a glucose/salt medium, to combine liposome treatment with other parenteral therapy.

Administration of the liposomal suspension is continued until a significant and measurable improvement of the disease is observed and wherein the levels of one or more of blood glucose, insulin, total cholesterol, LDL cholesterol, triglyceride, creatine kinase (CK), creatine kinase-MB (CK-MB), Hb-A1$_c$, lipoprotein (a), SGOT and SGPT fall back within the normal range or are significantly reduced.

A liposomal suspension is said to be administered in a "therapeutically effective amount" if the amount administered is physiologically significant. It is physiologically significant if its presence results in a detectable change in the physiology of a recipient subject. In particular, an amount of a liposomal suspension administered according to the present invention is physiologically significant if it results in a reduction of the levels of one or more of blood glucose, insulin, total cholesterol, LDL cholesterol, triglyceride, creatine kinase (CK), creatine kinase-MB (CK-MB), Hb-A1$_c$, lipoprotein (a), SGOT and SGPT.

EXAMPLES

The following examples illustrate various methods for preparing liposome compositions and using the compositions in the treatment method of the invention. The examples are intended to illustrate, but in no way limit, the scope of the invention.

Materials

Egg phosphatidylcholine (egg PC) may be purchased from Avanti Polar Lipids (Alabaster, Ala.) or Lipoid KG (Ludwigshafen, Germany). The egg PC was determined to be greater than 99% pure. The egg PC fatty acid composition was similar to the reported composition (Hertz, R. et al., *Chem. Phys. Lipid* (1975) 15:138). The main PCs of the preparation included 1-palmitoyl, 2-oleoyl PC and 1-palmitoyl, 2-linoleoyl PC.

Example 1

Preparation of Small Unilamellar Vesicles by Sonication

Egg PC dissolved in chloroform was placed in a 100 ml vessel and dried to a thin film under an inert atmosphere of nitrogen. Sterile saline was added to the lipid film to a final concentration of about 100 mg/ml, and the lipid film was hydrated with swirling. The resulting multilamellar vesicle (MLV) suspension was then bath sonicated for 1 hour using a Heat System Sonicator, Model 375W, at a power setting of 40-50% full value. The temperature of the suspension was maintained at about 4° C. during sonication. Large vesicles or MLVs were separated from the sonicated suspension by ultracentrifugation at 100,000 g for 1 hour (Barenholz, Y. et al., *Biochemistry* (1977) 16:2806). The remaining suspension of SUVs, having a concentration of about 100 mg/ml, was then filter sterilized.

Example 2

Preparation of Small Unilamellar Vesicles by Extrusion

Homogeneous small unilamellar vesicles (SUVs) of egg PC for human use with an average diameter of 65 nm±110 nm in size, in 0.15M NaCl, were prepared by extrusion using serial filtration through polycarbonate filters in a GH 76-400 pressure cell (Nucleopore) (Anselem, S., et al. In Gregoriadis, G. (ed). LIPOSOME TECHNOLOGY, pp. 501-524, CRC Press, Boca Raton, Fla. (1993)). These vesicles were empty SUVs.

Liposomal particle size was measured by Nicomp submicron laser particle sizer, by Quasielectric light scattering or comparable method. It can also be determined using a Coulter model N4 sub-micron particle analyzer equipped with a size distribution processor analyzer (Barenholz et al. In Gregoriadis, G. (ed), LIPOSOME TECHNOLOGY, pp. 524-607, CRC Press, Boca Raton, Fla. (1993)). The final extrusion step was through a 0.05 micrometer pore polycarbonate filter. Egg PC SUV's should be sterile and pyrogen-free and were sterilized by filtration through sterile 0.22 micrometer Millipore filters. They were packaged in 100 ml transparent moulded hydrolytic class I bottles, evacuated with nitrogen (N) with teflon coated standard stoppers (20 mm), and sealed with an Alu-cap with PE-disc.

The final product had a more than 99% purity. Total impurity values were NMT 1%, as measured by HPLC, GC/FID or comparable procedure. There was no single impurity greater than 0.3%. Total oxidation values were NMT 1%, as measured by UV/VIS spectrometry at 234, 268 and 278 nmn.

Below is some additional information relating to the final SUV liposomal product:

Lipid concentration: 5-20%, preferably 10%.

Chemical stability: Hydrolysis and peroxidation <1%.

Sterility: Passes FDA mandated standards for sterile solution. NMT 100 CFU per test sample. Conforms to USP standards.

Storage Conditions:

| Room Temperature (25° C., 60% RH) | Refrigerated Temperature (4° C., 45% RH) | Accelerated Temperature (40° C., 75% RH) |
|---|---|---|
| 1 week | 1 week | 1 week |
|  |  | 2 weeks |
| 1 month | 1 month | 1 month |
| 2 months | 2 months | 2 months |
| 3 months | 3 months | 3 months |
| 6 months | 6 months | 6 months |

Dose regimen: 50 mg-1 g total lipid/kg body weight.

Dosage form: White-yellowish translucent dispersion for intravenous infusion.

Contraindication: Allergy to eggs; having hemolytic red blood cells.

Adverse effects: No adverse effects found.

Liposomal Concentration: 100 mg/ml

Fatty acid composition of the egg PC (by weight):

| Palmitic acid | 35.6% |
|---|---|
| Stearic acid | 12.6% |
| Oleic Acid | 27.8% |
| Linoleic Acid | 17.9% |
| Arachidonic Acid | 9.5% |
| Docosapentaenoic acid | 0.7% |
| Docosahexaenoic acid | 2.0% |

Complete Liposomal Suspension:

| 10 g | phospholipids of which: |
|---|---|
| 9.9 g | egg PC, |
| 0.2-0.50 g | cholesterol and |
| 0.05-2.0 g | sphingomyelin |
| 0.012 g | Desferal ® |
| 0.9 g | sodium chloride |
| Sterile pyrogen-free water for injection to 100 ml. | |

Example 3

Alternative Preparation of Small Unilamellar Vesicles by Extrusion

Homogeneous small unilamellar vesicles (SUVs) of egg PC for human use with an average diameter of 60 nm±5 nm in size, were prepared by extrusion using filtration through polycarbonate membrane filters using an Aviston EmulsiFlex-C50 homogenizer with SuporCap™ and SuporDCF™ serial layer disposable filters (220 nm, 180 nm and 80 nm). These vesicles were empty SUVs.

Liposomal particle size was measured by Solvias A G, Basel, Switzerland submicron laser particle sizer, by Quasielectric light scattering or comparable method. It can also be determined using a Coulter model N4 sub-micron particle analyzer equipped with a size distribution processor analyzer (Barenholz et al. In Gregoriadis, G. (ed), LIPOSOME TECHNOLOGY, pp. 524-607, CRC Press, Boca Raton, Fla. (1993)). The final extrusion step was through a 0.08 µm pore polycarbonate membrane filter. Egg PC SUV's should be sterile, endotoxin (LAL)-free and pyrogen-free and were sterilized by filtration through sterile 0.22 µm pore polycarbonate membrane filters. They were packaged in 100 ml transparent moulded hydrolytic class II bottles, evacuated with nitrogen (N) with teflon coated standard stoppers (20 mm), and sealed with an Alu-cap with PE-disc.

The final product had a more than 99% purity. Total impurity values were NMT 1%, as measured by HPLC, GC/FID or comparable procedure. There was no single impurity greater than 0.3%. Total oxidation values were NMT 1%, as measured by UV/VIS spectrometry at 215, 233, and 279 nm.

Below are some additional information relating to the final SUV liposomal product:

Lipid concentration: 5-30%.

Chemical stability: Hydrolysis and peroxidation <1%.

Dosage form: White-yellowish translucent dispersion for intravenous infusion.

Sterility: Passes FDA mandated standards for sterile solution. NMT 100 CFU per test sample. Conforms to USP standards.

Storage Conditions:

| Refrigerated Temperature (4° C., 45% RH) |
|---|
| 1 month |
| 2 months |
| 3 months |
| 5 months |
| 6 months |
| 7 months |

Dose regimen: 50 mg-1 g total lipid/kg body weight.

Contraindication: allergy to eggs; having hemolytic red blood cells.

Adverse effects: No adverse effects found.

Fatty acid composition of the egg PC (by weight):

| Palmitic acid | 35.6% |
|---|---|
| Stearic acid | 12.6% |
| Oleic Acid | 27.8% |
| Linoleic Acid | 17.9% |
| Arachidonic Acid | 9.5% |
| Docosapentaenoic acid | 0.7% |
| Docosahexaenoic acid | 2.0% |

Complete Liposomal Suspension:

| 10 g | phospholipids of which |
|---|---|
| 9.0 g | Egg PC (Lipoid) |
| 0.2-0.5 g | cholesterol and |
| 0.05-2.0 g | sphingomyelin |
| 0.018 g | Desferal ® |
| 0.765 g | sodium chloride (Merck) |
| 0.279 g | L-histidine (Fluka) |
| Adjust pH to 6.5 with 1 M sodium hydroxide or 1 M hydrochloric acid | |
| 88.9945 g | Sterile pyrogen-free water (final volume: 100 ml), and nitrogen q.s. |

Example 4

Effects of Liposomal Treatment on an Insulin Resistant and Adult Onset Diabetic Patient Patient 1 is a sixty-two year old woman having a body size of 160 cm and a body weight of 45 kg. She has a preknown dysregulation of lipid metabolism and was diagnosed as an insulin-resistant metabolic patient for 17 years. For treatment, she was intravenously infused (20-50 drips/min) with two volumes of 90-ml per infusion (400 mg total lipid/kg body weight) of the complete liposomal suspension, prepared according to the procedure described in Example 3, six times within a 30 day period.

Patient 1 tolerated the liposomal therapy very well. She showed no signs or symptoms of any unwanted side effects. Even after several weeks of therapy, she did not experienced any subjective or clinical adverse symptoms. Her laboratory results showed elevated total cholesterol but her LDL and cholesterol levels decreased while her lipoprotein (a) level remained within the normal limits.

Before treatment, her glycated hemoglobin (Hb-A1$_c$) levels showed a slight increase or possible indication of glucose metabolic disturbance. After treatment, this level falls within the normal range.

TABLE 1

Laboratory Results for Patient 1 Before and After Treatment:

| Test | Reference Range | Before Treatment | After Treatment |
|---|---|---|---|
| Triglyceride | 0-200 mg/dl | 114 mg/dl | 71 mg/dl |
| Total Cholesterol | 100-200 mg/dl | 349 mg/dl | 312 mg/dl |
| LDL Cholesterol | 0-155 mg/dl | 219 mg/dl | 206 mg/dl |
| HDL Cholesterol | 35-55 mg/dl | 107 mg/dl | 92 mg/dl |
| Glucose | 55-115 mg/dl | 94 mg/dl | 92 mg/dl |
| CK | 0-195 U/l | 102 U/l | 84 U/l |
| CK-MB | 3.9 | N/A | N/A |
| Hb-A1$_c$ | 4.4-6.1 | 5.6 | 5.8 |
| Lipoprotein (a) | 0.3 | 0.11 g/L | 0.11 g/L |

Several weeks after the liposomal treatment, an Oral Glucose Tolerance Test was performed by application of an appropriate dosage of glucose. After two hours of glucose application, serologic glucose levels and insulin secretion were determined. Results showed that both glucose level and insulin secretion increased and reached a normalized level after two hours of glucose application. By contrast, results obtained from three years prior to the liposomal treatment revealed that both glucose level and insulin secretion failed to drop back to the normalized level after two hours of glucose application.

A comparison of Oral Glucose Tolerance Test before and after treatment is shown below:

TABLE 2

Oral Glucose Tolerance Test - Glucose and Insulin Values

| | Reference Range | Five Years Before Treatment | Three Years Before Treatment | After Treatment |
|---|---|---|---|---|
| Glucose, Fasting | 70-120 mg/dl | 93 | 96 | 96 |
| Glucose, 30 min | 70-180 mg/dl | 229 | 116 | 213 |
| Glucose, 60 min | 70-160 mg/dl | 176 | 173 | 217 |
| Glucose, 120 min | 70-130 mg/dl | 177 | 143 | 82 |
| Insulin, Fasting | 3-15 μU/ml | N/A | 3.2 | 3.6 |
| Insulin, 30 min | 10-74 μU/ml | N/A | 13.2 | 28.5 |
| Insulin, 60 min | 30-71 μU/ml | N/A | 35.4 | 105.6 |
| Insulin, 120 min | 10-48 μU/ml | N/A | 84.4 | 29.0 |

Therefore, treatment has improved the insulin resistance in the patient.

Example 5

Effects of Liposomal Treatment on a Metabolic Syndrome-X Patient

Patient No. 2 is a 51-year old man who has hypertension and a known metabolic disorder of lipids. He is overweight and has body size of 175 cm and a body weight of 90 kg. His initial values for total cholesterol and triglycerides were very high. However, his LDL-cholesterol and HDL-cholesterol were within normal limits. In addition, there was an increase of the liver enzyme, SGPT.

For treatment, patient No. 2 was intravenously infused (20-50 drips/min) with three-volumes of 90-ml per infusion (300 mg total lipid/kg body weight) of the complete liposomal suspension, prepared according to the procedure described in Example 3, six times within a period of 19 days.

During the treatment period, the patient's blood pressure, pulse frequency and oxygen load appeared normal. There were no subjective or clinical symptoms of unwanted effects.

Laboratory values after treatment revealed a decrease in total cholesterol and triglycerides, in addition to a partial normalization of SGOT (see Table 3), wherein treatment begins on May 10, 2002.

TABLE 3

Laboratory Results for Patient No. 2 Before and After Treatment:

| | Reference Range | Apr. 22, 2002 | May 10, 2002 | May 17, 2002 | Jun. 28, 2002 | Aug. 28, 2002 | Dec. 14, 2002 |
|---|---|---|---|---|---|---|---|
| Triglyceride | 0-200 mg/dl | 314 mg/dl | 798 mg/dl | 614 mg/dl | 342 mg/dl | 332 mg/dl | 195 mg/dl |
| Total Cholesterol | 100-200 mg/dl | 233 mg/dl | 244 mg/dl | 356 mg/dl | 218 mg/dl | 204 mg/dl | 197 mg/dl |
| LDL Cholesterol | 0-155 mg/dl | 125 mg/dl | 48 mg/dl | 185 mg/dl | 103 mg/dl | 94 mg/dl | 108 mg/dl |
| HDL Cholesterol | 35-55 mg/dl | 45 mg/dl | 36 mg/dl | 48 mg/dl | 47 mg/dl | 44 mg/dl | 50 mg/dl |
| Glucose | 55-115 mg/dl | 101 mg/dl | 85 mg/dl | 105 mg/dl | 110 mg/dl | 100 mg/dl | 107 mg/dl |
| CK | 0-195 U/l | 191 U/l | 238 U/l | 530 U/l | 298 U/l | 191 U/l | 185 U/l |
| CK-MB | 0-24 U/l | | 25 U/l | 23 U/l | | | |
| CRP | 0-0.5 mg/dl | | | 0.2 mg/dl | 0.0 mg/dl | 0.0 mg/dl | 0.0 mg/dl |
| SGOT | 0-50 U/l | 29.5 U/l | 26.8 U/l | 40.8 U/l | 29.6 U/l | 23.9 U./l | 27.2 g/l |
| SGPT | 0-41 U/l | 50.7 U/l | 46.6 U/l | 62.6 U/l | 57.5 U/l | 42.8 U/l | 39.5 g/l |
| Lipoprotein (a) | <0.3 g/dl | 0.688 g/l | 0.5 g/l | 0.59 g/l | 0.46 g/l | 0.42 g/l | 0.56 g/l |
| Fibrinogen | 200-400 mg/dl | 243 mg/dl | | | | | |
| Hb-A1$_c$ | 4.4-6.1% | | | 5.6% | | | |

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

What is claimed is:

1. A method of treating non-insulin dependent diabetes (NIDDM) or adult onset diabetes (AOD) and metabolic syndrome X in a mammal, comprising intravenously administering to said mammal a therapeutically effective amount of a liposomal suspension of small unilamellar vesicles (SUVs), wherein said SUVs predominantly comprises phospholipids selected from the group consisting of phosphatidycholine, phosphatidylglycerol and phosphatidylserine.

2. The method of claim 1, wherein said phosphatidylcholine is egg phosphatidylcholine.

3. The method of claim 1, wherein said phosphatidylcholine is 1-palmitoyl, 2-oleoyl phosphatidylcholine, 1-palmitoyl, 2-linoleoyl phosphatidylcholine or a mixture thereof.

4. The method claim 1, wherein said phosphatidylcholine has a transition temperature of less than about 37° C.

5. The method of claim 4, wherein said transition temperature is in the range of about −10 to 24° C.

6. The method claim 1, wherein said lipoprotein SUVs further comprise sphingomyelin, cholesterol or other sterols, in an amount less than about 40 mole percent.

7. The method of claim 1, wherein said SUVs are empty.

8. The method of claim 1, wherein said liposomal suspension is administered one to three times per week to said mammalian subject at a dose for each administration of about 50 mg-1 g total lipid/kg body weight.

9. The method of claim 8, wherein said dose is about 200-450 mg total lipid/kg body weight.

10. The method of claim 1, wherein said SUVs are administered by intravenous injection or intravenous infusion.

\* \* \* \* \*